US00PP08325P

United States Patent [19]

Vletter

[11] Patent Number: Plant 8,325

[45] Date of Patent: Jul. 27, 1993

[54] LILY PLANT NAMED CASCADE

[75] Inventor: Floris Vletter, Rijnsburg, Netherlands

[73] Assignee: Gebr. Vletter & J.A., Rijnsburg, Netherlands

[21] Appl. No.: 795,957

[22] Filed: Nov. 21, 1991

[51] Int. Cl.[5] ..... A01H 5/00

[52] U.S. Cl. ..... Plt./87.4

[58] Field of Search ..... Plt./87.4

[56] References Cited

PUBLICATIONS

Lesli, A. C. 'Cascade' *The International Lily Register* 1982 The Royal Horticultural Society, London, p. 48.

*Primary Examiner*—James R. Feyrer

*Attorney, Agent, or Firm*—Foley & Lardner

[57] ABSTRACT

A new and distinct cultivar of lily plant named Cascade, characterized by its flower color which consists of a main color of light pink, a deeper red-purple color along and to either side of the midvein, and white edges and tips; long stems, and elliptical red-purple spots on each flower.

1 Drawing Sheet

The present invention comprises a new and distinct cultivar of lily, botanically known as Lilium, known commercially as Lilium oriental hybrid, and hereinafter referred to by the cultivar name Cascade. The parents were oriental varieties belonging to division VII(b) described in "Classification of Lily Cultivars into Divisions" published by Victoria Mathews, The Royal Botanic Gardens, Kew (1989).

The new cultivar is a product of a planned breeding program which had the primary objective of creating new lily cultivars having upright flowers and unique bright colors.

The new cultivar was originated from a hybridization made by the inventor in a controlled breeding program in Rijnsburg, The Netherlands in 1979. The female parent was the cultivar Stargazer. The male parent was an unnamed seedling.

The new cultivar was discovered and selected as one flowering plant within the progeny of the stated cross by the inventor in July 1979 in a controlled environment in Rijnsburg, The Netherlands.

The first act of asexual reproduction of the new cultivar was accomplished by the inventor when scales were taken from the initial selection in 1983 in a controlled environment in Rijnsburg, The Netherlands.

Horticultural examination of selected units has demonstrated that the combination of characteristics as herein disclosed for the new cultivar are firmly fixed and are retained through successive generations of asexual reproduction.

The new cultivar has not been observed under all possible environmental conditions. The phenotype may vary somewhat with variations in environment such as temperature, light intensity, and day length, without, however, varying in the genotype. The following observations, measurements and comparisons describe plants grown in Wageningen and Rijnsburg, The Netherlands under greenhouse conditions which approximate those generally used in commercial practice.

The following traits have been repeatedly observed and are determined to be basic characteristics of Cascade which in combination distinguish this lily as a new and distinct cultivar.

1. Bright pink main flower color;

2. A much darker red-purple color extends along and to either side of the midvein of each petal, terminating before the tip;

3. The edges and tips of the flower are white;

4. The flowers are carried on long stems.

Of the many commercial cultivars known to the present inventor, the most similar in comparison to the new cultivar is Stargazer. In comparison to Stargazer, Cascade has a brighter pink flower color and longer stems. When flowering is forced under natural light, Cascade produces an inflorescence approximately 3 days earlier than Stargazer, grown under the same conditions. Cascade is fertile.

The accompanying color photographic drawing shows typical flower characteristics of the new cultivar, with colors being as true as possible with illustrations of this type. The photograph comprises a front perspective view of two open flowers and several buds at various stages.

In the following description, color references are made to The Royal Horticultural Society (RHS) Colour Chart. The color values were determined at Wageningen in 1988–1989 and at Rijnsburg in July 1991.

Origin: Seedling.

Parentage:

*Seed parent.*—Stargazer.

*Pollen parent.*—Unnamed seedling.

Classification:

*Botanical.*—Lilium.

*Commercial.*—Oriental hybrid.

The plant:

*Form.*—A single stem carrying numerous pedicels alternately arranged.

*Height.*—Approximately 140 cm at time of opening of anthers of first flower.

*Growth habit.*—Vigorous.

*Stem.*—Circular in transverse section; color 142C; internodal length uniform (4.5 cm); anthocyanin pigmentation present.

*Foliage.*—Quantity: 50–60 leaves depending on growing conditions. Size of Leaf: Mature leaves are long (18 cm) and wide to very wide (5.5 cm). Shape of leaves: Small, ovate. Texture: Smooth with weak glossiness; no pubescence. Color: Medium green 137A.

*Bulbs.*—Size: Outlet 6–30 cm. Color: White.

*Roots.*—Both stem and contractile present.

The bud:

*Form.*—Tapering (like a lancet).

*Size.*—14 cm in length prior to opening.

*Opening.*—Unfolds normally.

*Color.*—63C (Mature).

*Tepals.*—Folded, three visible.

The flower:

*Blooming habit.*—Raceme articulated from node to node.

*Size.*—Approximately 20 cm in diameter depending on growing conditions.

*Borne.*—Upright to almost horizontal.

*Shape.*—Generally in form of hexagonal star and bowl shaped in cross-section.

*Tepalage.*—Number of tepals: Six. Arrangement: Three inner and three outer each with marginal undulation. Color: Upper Surface: Main Color 63C; along and to either side of midvein, 63A; somewhat transparent. Lower surface: 63C; along axis 63A. Spotting or marking: Many dark pink spots along each tepal; each spot is elliptically shaped, approximately 1 mm wide and 2.5 mm long.

*Nectaries and papillae.*—Present.

*Pedicel.*—Length: 10 cm. Color: Medium green. Form: Slightly curved.

*Texture.*—Papillose.

*Disease resistance.*—No disease problems noted to date.

*Fragrance.*—Present; strong.

*Lasting quality.*—Excellent.

Reproductive organs:

*Stamens, anthers.*—Arrangement: Anthers form a generally circular pattern. Length: Long (8 cm). Number: Six. Filaments: White at the base, light green at the top.

*Pollen color.*—Dark brown.

*Anther color.*—Dark pink.

*Pistils.*—Long to very long, 10 cm; light to medium green in color.

*Stigma.*—Triangular; purple stigma.

*Ovaries.*—Triangular in shape; other characteristics typical of oriental lily varities.

I claim:

1. A new and distinct cultivar of lily plant named Cascade, as illustrated and described.

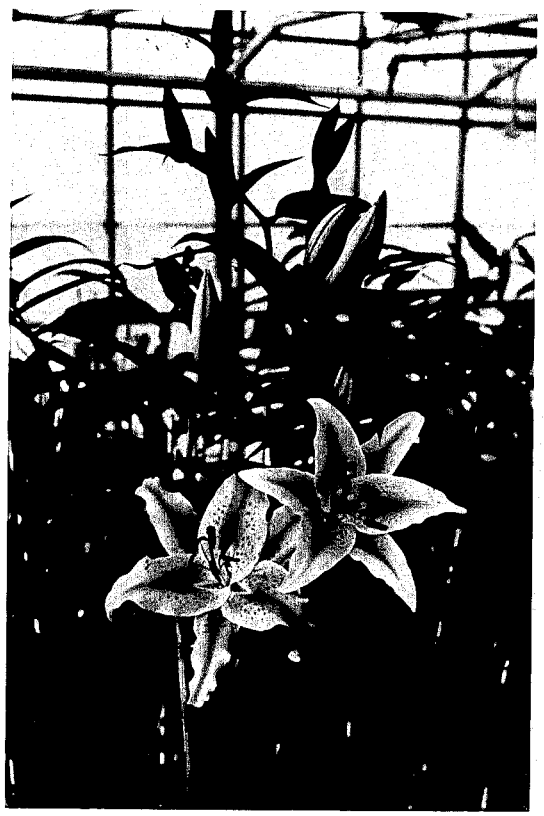

* * * * *